United States Patent
Ross

(10) Patent No.: US 11,408,851 B2
(45) Date of Patent: Aug. 9, 2022

(54) ELECTROCHEMICAL METHOD TO DETERMINE THE SENSITIVITY OF A GAS SENSOR BY PULSE SEQUENCES

(71) Applicant: MSA Europe GmbH, Jona (CH)

(72) Inventor: Sebastian Ross, Berlin (DE)

(73) Assignee: MSA Europe GmbH, Jona (CH)

( * ) Notice: Subject to any disclaimer, the term of this patent is extended or adjusted under 35 U.S.C. 154(b) by 865 days.

(21) Appl. No.: 16/314,914

(22) PCT Filed: Jul. 11, 2017

(86) PCT No.: PCT/EP2017/067387
§ 371 (c)(1),
(2) Date: Jan. 3, 2019

(87) PCT Pub. No.: WO2018/011200
PCT Pub. Date: Jan. 18, 2018

(65) Prior Publication Data
US 2019/0170679 A1   Jun. 6, 2019

(30) Foreign Application Priority Data

Jul. 12, 2016 (DE) .................... 10 2016 212 664.4

(51) Int. Cl.
*G01N 27/404* (2006.01)
*G01N 33/00* (2006.01)
*G01N 27/30* (2006.01)

(52) U.S. Cl.
CPC ....... *G01N 27/4045* (2013.01); *G01N 27/301* (2013.01); *G01N 27/404* (2013.01);
(Continued)

(58) Field of Classification Search
CPC ............. G01N 27/404; G01N 27/4045; G01N 27/407; G01N 33/0006; F01N 2900/0416
See application file for complete search history.

(56) References Cited

U.S. PATENT DOCUMENTS

| | | | |
|---|---|---|---|
| 5,202,637 A | 4/1993 | Jones | |
| 6,049,283 A | 4/2000 | Lindsay | |

(Continued)

FOREIGN PATENT DOCUMENTS

| | | |
|---|---|---|
| CN | 103364470 A | 10/2013 |
| CN | 104270011 A | 1/2015 |

(Continued)

OTHER PUBLICATIONS

Yao Wang, "Frequency Domain Characterization of Signals," course handout for EE3414 Multimedia Communication Systems—I, downloaded Dec. 6, 2021 from https://eeweb.engineering.nyu.edu/~yao/EE3414/signal_freq.pdf (Year: 2006).*

*Primary Examiner* — Alexander S Noguerola
(74) *Attorney, Agent, or Firm* — Jones Day

(57) ABSTRACT

An electrochemical method for determining the sensitivity of at least one gas sensor. The method includes applying at least two electrical pulses to at least two parts of at least two electrodes of the gas sensor, recording the change of the current pattern induced in the at least two electrodes by the at least two pulses over time, calculating at least one value for the sensor sensitivity by applying an algorithm to the current pattern induced by the at least two pulses, and comparing the calculated sensitivity value to known gas sensitivity calibration data.

20 Claims, 3 Drawing Sheets

(52) U.S. Cl.
CPC ....... *G01N 33/004* (2013.01); *G01N 33/0006* (2013.01); *G01N 33/007* (2013.01)

(56) References Cited

U.S. PATENT DOCUMENTS

| | | | |
|---|---|---|---|
| 6,200,443 B1 | 3/2001 | Shen et al. | |
| 6,404,205 B1 | 6/2002 | Kitamura | |
| 7,060,169 B2 * | 6/2006 | Rohrl | H01M 8/188 204/431 |
| 7,413,645 B2 | 8/2008 | Scheffler | |
| 8,097,146 B2 * | 1/2012 | Smith | G01N 27/404 205/775 |
| 9,213,016 B1 | 12/2015 | Stetter et al. | |
| 9,291,608 B2 * | 3/2016 | Herzl | G01N 33/0006 |
| 9,546,976 B2 | 1/2017 | Seyr et al. | |

FOREIGN PATENT DOCUMENTS

| | | |
|---|---|---|
| DE | 4212792 A1 | 10/1993 |
| EP | 0039549 A2 | 11/1981 |
| EP | 1039293 A1 | 9/2000 |

\* cited by examiner

----- ambient  ── -4 weeks 80°C  - - -10 weeks at 80°C  ──── 3 month at 80°C

----- before  ──── recovery  - - - after ppmh

ELECTROCHEMICAL METHOD TO DETERMINE THE SENSITIVITY OF A GAS SENSOR BY PULSE SEQUENCES

CROSS-REFERENCE TO RELATED APPLICATIONS

This applications is the United States national phase of International Application No. PCT/EP2017/067387 filed Jul. 11, 2017, and claims priority to German Patent Application No. 10 2016 212 664.4 filed Jul. 12, 2016, the disclosures of which are hereby incorporated in their entirety by reference.

BACKGROUND OF THE INVENTION

Field of the Invention

The present invention relates to an electrochemical method for determining the sensitivity of a gas sensor.

Description of Related Art

Electrochemical gas sensors or gas detectors typically comprise at least two electrodes, at least one of which is a gas diffusion electrode (working electrode) and the other one is a counter electrode. Both electrodes are in ionic contact via an appropriate electrolyte, such as a solid electrolyte or liquid electrolyte, whereby the use of ionic liquids as electrolytes became prominent in the past two years.

Various manufacturers of gas sensors include some means of monitoring the presence of an electrochemical gas sensor in determining its serviceability. One common method is to generate a suitable target gas (either the analyte of interest or a suitable simulant) and monitor the response of the sensor to the generated gas. However, this technique has several disadvantages including complexity and ambiguity.

In a number of current sensors, the sensor serviceability is determined by electronic testing. For example, U.S. Pat. No. 6,049,283 describes a method of detecting the presence of a serviceable gas sensor by measuring the electronic noise in the output of the sensor amplifier. U.S. Pat. No. 5,202,637 describes a method for detecting the presence of an electrochemical gas sensor by applying a potential pulse or a periodically varying potential to the sensor. The output current of the sensors is monitored. If the current is detected in response to the potential signal, then a sensor is present.

A further approach is disclosed in U.S. Pat. No. 7,413,645. Here the output of an electrochemical sensor is adjusted by simulating the presence of an analyte gas electronically, measuring a response of the sensor to the electronic simulation by applying one current pulse (5 mV for 20 seconds) and adjusting an output of the sensor as a function of the measured response to the electronic simulation. This testing method provides a real-time measure of sensor performance. The electronic interrogation affects the sensor in generally the same way as exposure to target gas does. Said method causes a current to flow through the sensor in the same manner as the appearance of target gas at the working electrode. However, this method has been shown only to be applicable to certain gas sensors.

In particular, it has been shown that said method cannot be used for gas sensors with electrolytes comprising certain additives for improving sensitivity and stability. For example, when applying the method described in U.S. Pat. No. 7,413,645 to a gas sensor for detecting $Cl_2$, comprising an ionic liquid with an inorganic additive, no correlation between sensitivity calculated by electronic stimulation and measured gas sensitivity is found.

Thus, there is a need to provide a method for testing gas sensors that can be applied to gas sensors with an electrolyte comprising any type of disturbing compounds, which may cover the active surface of the electrodes, such as additives. The testing method should be reliable and applicable to a broad spectrum of gas sensors.

SUMMARY OF THE INVENTION

Generally, provided is an electrochemical method for determining the sensitivity of at least one gas sensor.

In one preferred and non-limiting embodiment or aspect, the electrochemical method for determining the sensitivity of at least one gas sensor includes applying at least two electrical pulses to at least two parts of at least two electrodes of the gas sensor; recording a change of a current pattern induced in the at least two electrodes by the at least two pulses over time; calculating at least one value for the sensor sensitivity by applying an algorithm to the current pattern induced by the at least two pulses; and comparing the calculated sensitivity value to known gas sensitivity calibration data.

In one preferred and non-limiting embodiment or aspect, the at least two pulses can be voltage pulses.

In one preferred and non-limiting embodiment or aspect, the at least two pulses can be varied by one of the following pulse parameters: pulse height (mV), pulse length (sec), and type of pulse.

In one preferred and non-limiting embodiment or aspect, the parameters can be the same or different for each of the at least two pulses.

In one preferred and non-limiting embodiment or aspect, the at least two electrical pulses can be applied in opposite directions to the gas sensor.

In one preferred and non-limiting embodiment or aspect, a sequence of more than two electrical pulses, in particular three, four or more pulses, can be applied to the at least one gas sensor.

In one preferred and non-limiting embodiment or aspect, the current pattern induced by the at least two pulses can be described by at least 2 parameters, preferably by at least 5 or 7 or 8 parameters.

In one preferred and non-limiting embodiment or aspect, the current pattern induced by the at least two pulses can be described by one of the following parameters: a maximal or minimal peak (corresponding to pulse height) of first pulse P1; a resting peak of a first pulse P1 (RestPeak 1); an area under curve of the first pulse (AUC1); a maximal or minimal peak (corresponding to pulse height) of a second pulse P2; a resting peak of the second pulse P2 (RestPeak 2); and an area under curve of the second pulse (AUC2).

In one preferred and non-limiting embodiment or aspect, the at least one algorithm for calculating the at least one value for the sensor sensitivity can be generated based on the parameters, in particular the at least 2 parameters, of the current pattern induced by the at least two pulses.

In one preferred and non-limiting embodiment or aspect, the gas sensitivity calibration data can be previously obtained from the same gas sensor type.

In one preferred and non-limiting embodiment or aspect, the at least one gas sensor can comprise an electrolyte selected from a group comprising: at least one ionic liquid with at least one additive portion; an aqueous salt solution, in particular an aqueous LiCl solution; a mineral acid, in particular $H_2SO_4$, $H_3PO_4$; a base, in particular KOH; and an organic salt solution, in particular $LiPF_6$ in dimethylcarbonate glycol and/or ethylenecarbonate glycol.

In one preferred and non-limiting embodiment or aspect, the at least one additive portion can comprise at least one organic additive, at least one organometallic additive, or at least one inorganic additive.

In one preferred and non-limiting embodiment or aspect, the sensor can comprise at least two electrodes in electrical contact with the ionic liquid, the electrodes being separated from one another by a separator or by space.

In one preferred and non-limiting embodiment or aspect, the electrodes can comprise independently, the same or different: a metal selected from the group of Cu, Ni, Ti, Pt, Ir, Au, Pd, Ag, Ru, Rh, and an oxide of Cu, Ni, Ti, Pt, Ir, Au, Pd, Ag, Ru, or Rh, mixtures thereof, or carbon, such as graphite, in particular graphite, Cu, Ag.

In one preferred and non-limiting embodiment or aspect, the gas sensor can be adapted for the detection of gases selected from the group of acid gases, basic gases, neutral gases, oxidizing gases, reducing gases, halogen gases, halogen vapors, and hydride gases, in particular selected from the group of $F_2$, $Cl_2$, $Br_2$, $I_2$, $O_2$, $O_3$, $ClO_2$, $NH_3$, $SO_2$, $H_2S$, CO, $CO_2$, NO, $NO_2$, $H_2$, HCl, HBr, HF, HCN, $PH_3$, $AsH_3$, $B_2H_6$, $GeH_4$, and $SiH_4$.

Various preferred and non-limiting embodiments or aspects of the present invention will now be described and set forth in the following numbered clauses:

Clause 1: An electrochemical method for determining the sensitivity of at least one gas sensor comprises: applying at least two electrical pulses to at least two parts of at least two electrodes of the gas sensor, recording a change of a current pattern induced in the at least two electrodes by the at least two pulses over time, calculating at least one value for the sensor sensitivity by applying an algorithm to the current pattern induced by the at least two pulses, and comparing the calculated sensitivity value to known gas sensitivity calibration data.

Clause 2: The method according to clause 1, wherein the at least two pulses can be voltage pulses.

Clause 3: The method according to clause 1 or 2, wherein the at least two pulses can be varied by one of the following pulse parameters: pulse height (mV), pulse length (sec), and type of pulse.

Clause 4: The method according to any one of clauses 1-3, wherein the parameters can be the same or different for each of the at least two pulses.

Clause 5: The method according to any one of clauses 1-4, wherein the at least two electrical pulses can be applied in opposite directions to the gas sensor.

Clause 6: The method according to any one of clauses 1-5, wherein a sequence of more than two electrical pulses, in particular three, four or more pulses, can be applied to the at least one gas sensor.

Clause 7: The method according to any one of clauses 1-6, wherein the current pattern induced by the at least two pulses can be described by at least 2 parameters, preferably by at least 5 or 7 or 8 parameters.

Clause 8: The method according to any one of clauses 1-7, wherein the current pattern induced by the at least two pulses can be described by one of the following parameters: a maximal or minimal peak (corresponding to pulse height) of first pulse P1, a resting peak of a first pulse P1 (RestPeak 1), an area under curve of the first pulse (AUC1), a maximal or minimal peak (corresponding to pulse height) of a second pulse P2, a resting peak of the second pulse P2 (RestPeak 2), and an area under curve of the second pulse (AUC2).

Clause 9: The method according to any one of clauses 1-8, wherein the at least one algorithm for calculating the at least one value for the sensor sensitivity can be generated based on the parameters, in particular the at least 2 parameters, of the current pattern induced by the at least two pulses.

Clause 10: The method according to any one of clauses 1-9, wherein the gas sensitivity calibration data can be previously obtained from the same gas sensor type.

Clause 11: The method according to any one of clauses 1-10, wherein the at least one gas sensor can comprise an electrolyte selected from a group comprising: at least one ionic liquid with at least one additive portion; and an aqueous salt solution, in particular an aqueous LiCl solution; a mineral acid, in particular $H_2SO_4$, $H_3PO_4$; a base, in particular KOH; and an organic salt solution, in particular $LiPF_6$ in dimethylcarbonate/ethylencarbonate, glycol.

Clause 12: The method according to any one of clauses 1-11, wherein the at least one additive portion can comprise at least one organic additive, at least one organometallic additive, or at least one inorganic additive.

Clause 13: The method according to any one of clauses 1-12, wherein the sensor can comprise at least two electrodes in electrical contact with the ionic liquid, the electrodes being separated from one another by a separator or by space.

Clause 14: The method according to any one of clauses 1-13, wherein the electrodes can comprise independently, the same or different: a metal selected from the group of Cu, Ni, Ti, Pt, Ir, Au, Pd, Ag, Ru, Rh; an oxide of Cu, Ni, Ti, Pt, Ir, Au, Pd, Ag, Ru, or Rh, mixtures thereof, or carbon, such as graphite, in particular graphite, Cu, Ag.

Clause 15: The method according to any one of clauses 1-14, wherein the gas sensor can be adapted for the detection of gases selected from the group of acid gases, basic gases, neutral gases, oxidizing gases, reducing gases, halogen gases, halogen vapors, and hydride gases, in particular selected from the group of $F_2$, $Cl_2$, $Br_2$, $I_2$, $O_2$, $O_3$, $ClO_2$, $NH_3$, $SO_2$, $H_2S$, CO, $CO_2$, NO, $NO_2$, $H_2$, HCl, HBr, HF, HCN, $PH_3$, $AsH_3$, $B_2H_6$, $GeH_4$, and $SiH_4$.

More specifically, disclosed herein is an electrochemical method for determining the sensitivity of at least one gas sensor, comprising
  applying at least two electrical pulses (as electronic simulation of the presence of an analyte gas) to at least two parts of at least two electrodes of the gas sensor,
  recording the change of the current pattern induced in the at least two electrodes by the at least two pulses over time,
  calculating at least one value for the sensor sensitivity by applying an algorithm to the current pattern induced by the at least two pulses, and
  comparing the calculated sensitivity value to known gas sensitivity calibration data.

The present method allows to establish a correlation between the change of a pulse response or current response (as a model of response parameter) and the gas sensor sensitivity. The present method allows furthermore for a correction of sensitivity in case of gas sensors that are currently not accessible for electrochemical correction. The influence of additives in electrochemical gas sensors can be overcome by the present method.

The application of at least two pulses to the electrodes enables a specific interaction with additives and complex electrode systems in electrochemical sensors. It is believed that the first electrical pulse serves for cleaning the electrode surface from any interfering deposits and removing any deposits of additives or other compounds occupying the active electrode surface. The first and second electrical pulse induces a current pattern and the response of the sensor to the electronic simulation is measured. A specific algorithm is applied to the measured response or output of the sensor that allows for calculating sensitivity of the sensor to the electrical pulse. The sensitivity calculated by said algorithm corresponds to the gas sensitivity of the gas sensor. Since the current pattern (characterized by certain specific parameters) changes over time and conditions such as humidity, aging, temperature or gassing history the present method allows for following the change of sensitivity of the gas sensor over time and determining the general functionality of the sensor.

In a preferred embodiment of the present method the at least two electrical pulses applied are voltage pulses.

Furthermore, the at least two pulses can be varied by one of the following pulse parameters pulse height (mV), pulse length (sec) and type of pulse. Said parameters can be the same or different for each of the at least two pulses. In a variant, the pulse height of the at least two pulses can be in a range between 0.1 and 100 mV, preferably between 1 and 80 mV, more preferably between 5 and 50 mV, even more preferably between 10 and 30 mV. The pulse length of the at least two pulses can be, for example, in a range between $1/100$ sec and 10 sec, preferably between $1/18$ and 5 sec, most preferably between $1/10$ and 1 sec. Also, the type of pulse can be varied and may be a rectangular pulse or a ramp pulse. The pulse may also be an alternating current signal with various frequencies and amplitudes.

In a preferred embodiment of the present method, the at least two electrical pulses are applied in opposite directions to the gas sensor.

It is also possible that a sequence of more than two electrical pulses, in particular three, four or more pulses, is applied to the at least one gas sensor.

If a sequence of more than two pulses is applied than the pulses may be applied in alternating directions; i.e., a first pulse is applied in one direction, the second pulse is applied in the opposite direction and a third pulse is applied again in the direction of the first pulse and so forth.

In a preferred embodiment, a first pulse with a pulse height 5-15 mV, preferably 10 mV is applied for 1-10 sec, preferably for 1-5 sec, most preferably for 1-2 sec, and a second opposite pulse with a pulse height of 10-50 mV, preferably 20-40 mV, most preferably 30 mV is applied for 1-10 sec, preferably for 1-5 sec, most preferably for 1-2 sec.

As mentioned above, the electrical pulses induce a current pattern in the gas sensor. Said current pattern induced by the at least two pulses can be described by specific parameters, in particular by at least 2 parameters, preferably at least 4 parameters. The number of parameters depends thereby on the number of pulses applied to the sensor. For example, in case a sequence of two pulses is applied then the current pattern can be described using at least 3 parameters, preferably 8 parameters.

In a preferred embodiment of the present method, the current pattern induced by the at least two pulses can be described by one of the following parameters: a maximal or minimal peak (corresponding to pulse height) of first pulse P1, a resting peak of first pulse P1 (RestPeak 1), the area under curve of first pulse (AUC1), a maximal or minimal peak (corresponding to pulse height) of second pulse P2, a resting peak of second pulse P2 (RestPeak 2), and the area under curve of second pulse (AUC2).

The second pulse is preferably followed by at least a partial recovery of the sensor (i.e., the sensor reaction gets back to its original potential). The additional parameters of recovery may also be used for describing the current pattern: maximal or minimal peak and area under curve of third pulse (AUC3).

The parameters describing the induced current pattern form the base for the above-mentioned algorithm.

The algorithm provides a mathematical connection between at least two pulse peaks. At least two parameters generated by at least two pulses are used, i.e., at least one parameter assigned to at least one pulse. In particular, one parameter of a first pulse required for purifying the electrode and one parameter of a second pulse for testing are required for the algorithm.

Thus, in a preferred variant of the present method the at least one algorithm for calculating the at least one value for the sensor sensitivity is generated based on the parameters, in particular at least two parameters, of the current pattern induced by the at least two pulses. Said algorithm comprises calculating a difference in the response of the sensor before and after the simulation based on the at least two parameters characterizing the current pattern induced by the at least two pulses.

The algorithm is based on the above-mentioned parameters that are combined with different constants and factors obtained by regression. Depending on the number of parameters and constants used by the algorithm, a complex algorithm and/or a simplified algorithm may be applied. Irrespective if a complex or a simplified algorithm is applied the sensitivity calculated by said algorithm corresponds to the gas sensitivity of the gas sensor.

The correlation between gas sensitivity and sensitivity calculated by the algorithm is influenced by the number of the pulse parameters used for generating the algorithm. As mentioned above, at least two parameters of at least two different pulses are required for providing a meaningful algorithm. However, the more pulse parameters for creating the algorithm are used the better the correlation to the gas sensitivity. For example, a better correlation to the gas sensitivity is obtained using 4, 5, 6, 7, or 8 parameters.

Based on the numbers of pulse parameters used, different types of algorithms can be established. When using a high number of parameters (such as 7 or 8), a first model of the best regression (I) can be established, when using a lower number of parameters (such as 4 or 5) a second simplified model (II) may be established.

The algorithm is obtained in the following manner: in a first step a first calibration of the sensor is carried out comprising the recording of a first voltage pulse and gassing with a target gas (such as chlorine) in order to determine the actual gas sensitivity of the sensor. Different parameters (at time t=0) of the current response curve are determined. This test is repeated in regular intervals, i.e., applying the pulse and measuring the sensitivity by target gas calibration, and values for gas sensor sensitivity and the parameters (at time t) of the current response to the pulse are determined. A difference of the parameter values at time t and t0 is subsequently calculated in order to follow the change of the value over time. Said differences are used for the actual sensitivity calculation. The following general equation is applied:

$$\Delta\ parameter = parameter(t1) - parameter(t0)$$

The set of $\Delta$ parameter is then subjected to a multi-linear regression in order to determine a correlation between the change of sensitivity and the change of parameters. Thereby, the focus can be directed to the best possible regression (I) or to a simplified model (II). The algorithms applied in each case are described in detail in the examples. Both models provide a good correlation between measured and calculated sensitivity.

Thus, the induced current pattern is compared to a reference pattern based on actual gas sensitivity. When comparing both patterns a correlation between the calculated sensitivity (based on electrical pulse stimulation) and the measured sensitivity is detectable. For example, there is corresponding progress of calculated and measured sensitivity that allows also to differentiate between error modes of the sensor such as storage of the gas sensor at increased temperatures over a longer period of time or an overload of the sensor with a gas to be detected.

In one embodiment, the at least one gas sensor used in the present method comprises an electrolyte comprising at least one ionic liquid with at least one additive portion. In other embodiments, the gas sensor may comprise an electrolyte selected from a group comprising aqueous salt solutions, in particular an aqueous LiCl solution; a mineral acid, in particular $H_2SO_4$, $H_3PO_4$; a base, in particular KOH; organic salt solution, in particular $LiPF_6$ in dimethylcarbonate glycol and/or ethylenecarbonate glycol.

In case the electrolyte comprises an ionic liquid said ionic liquid can, for example, include at least one cation which is selected from the group of imidazolium, pyridinium, guanidinium, the cation being unsubstituted or substituted with at least one of an aryl group or a C1 to C4 alkyl group, the aryl group and the C1 to C4 alkyl group being unsubstituted or substituted with at least one of a halogen, a C1 to C4 alkyl group, a hydroxyl group or an amino group. In several embodiments, the ionic liquid includes at least one of an imidazolium cation, a C1 to C4 alkyl imidazolium cation, a pyridinium cation, or a C1 to C4 alkyl pyridinium cation.

The ionic liquid can, for example, include at least one anion selected from the group of a halide anion (i.e., chloride, iodide, bromide, or fluoride), a nitrate anion, a nitrite anion, a tetrafluoroborate anion, a hexafluorophosphate anion, a polyfluoroalkane sulphonate anion, a bis(trifluoromethylsulfonyl)imide anion, an alkyl sulphate anion, an alkane sulphonate anion, an acetate anion, and an anion of a fluoroalkane acid.

In several embodiments, the ionic liquid includes at least one anion selected from the group of a C1-C6 alkyl sulphate anion and a C1-C6 alkane sulphonate anion. The ionic liquid can, for example, include at least one anion from the group of a methyl sulphate anion, an ethyl sulphate anion, a butyl sulphate anion, a methanesulphonate anion, an ethanesulphonate anion, and a butanesulphonate anion. In several embodiments, the ionic liquid comprises 1-ethyl-3-methyl-imidazolium methanesulphonate or ethylammonium nitrate.

In an embodiment, the ionic liquid electrolyte includes an additive portion comprising at least one organic additive, and organometallic additive or an inorganic additive. In general, the organic additive, the organometallic additive and/or the inorganic additive are not ionic liquids. The performance of gas sensors can be improved significantly with regard to sensitivity, response time, selectivity, and robustness by adding such additives to the ionic liquid forming an electrolyte.

The additive portion or the additives can be included within the ionic liquid in an amount of 0.05 to 15 weight %. Organic additives can, for example, be included in an amount of 0.05 to 5.0 weight %. Inorganic additives can be included in an amount of 0.05 to 5.0 weight %. Organometallic additives can be included in an amount of 0.05 to 5 weight %.

Mixtures of various additives can also be used in the electrolyte. The additive mixture can be a mixture of various additives of the same group (for example, a mixture of various organic additives). The mixture of different additives can also include additives from different groups (for example, mixture of organic and inorganic additives). The cross sensitivity patent of sensors can be adapted to specific requirements by using mixtures of various additives.

The at least one organic additive can be selected from the group comprising imidazole, a C1 to C4 alkyl imidazole, pyridine, a C1 to C4 alkyl pyridine, pyrrole, a C1 to C4 alkyl pyrrole, pyrazole, a C1 to C4 alkyl pyrazole, pyrimidine, a C1 to C4 alkyl pyrimidine, guanine, a C1 to C4 alkyl guanine, uric acid, benzoic acid, a porphyrin, or a porphyrin derivative.

The at least one organometallic additive is selected from the group of organometallic porphyrins and organometallic porphyrin derivatives. The organometallic porphyrin can be selected from the group of porphyrins with at least one meso-alkyl substituent, at least one β-alkyl substituent, at least one aryl substituent, and their derivatives. Organometallic porphyrin derivatives can be selected from the group of a metal phthalocyanine with $Mn^{2+}$, $Cu^{2-}$, $Fe^{2+/3+}$, or $Pb^{2+}$ as the metal cation.

The at least one inorganic additive can be selected from the group of an alkali halide, an ammonium halide, a C1 to C4 alkyl ammonium halide, a transition metal salt, and a lead salt. The transition metal salt can be selected from the group of salts of $Mn^{2+}$, $Mn^{3+}$, $Cu^{2+}$ $Ag^+$, $Cr^{3+}$, $Ci^{6+}$, $Fe^{2+}$, or $Fe^{3+}$ and the lead salt is a salt of $Pb^{2+}$. In several embodiments, the at least one inorganic additive is selected from the group of lithium bromide, lithium iodide, ammonium iodide, tetramethylammonium iodide, tetraethylammonium iodide, tetrapropylammonium iodide, tetrabutylammonium iodide, tetrabutylammonium bromide, manganese(II) chloride, manganese(II) sulphate, manganese(II) nitrate, chrom(III) chloride, alkali chromates, iron(II) chloride, iron(III) chloride, and lead(II) nitrate.

The electrolyte can be substantially absorbed in a solid material. At least a part of the additive portion can be immobilized upon a solid support, upon the solid material and/or upon at least one of the electrodes. In several embodiments, the solid material can be a powdered silicate having an average particle size of at least 5 μm, at least 50 μm, or at least 75 μm, having a specific surface area of at least 50 $m^2/g$, at least 100 $m^2/g$ or at least 150 $m^2/g$ and a $SiO^2$ content of at least 95% by weight. In other embodiments, the liquid electrolyte is absorbed upon a fibrous nonwoven solid material in the form of the glass fibre.

In a further embodiment of the present method, the gas sensor can for example comprise at least two electrodes in electrical contact with the ionic liquid, where in the electrodes are separated from one another by a separator or by space. Sensors including two, three, or four and more electrodes are possible. In some embodiments, the sensors include two electrodes of the electrodes and housing.

The housing comprises at least one opening through which the gas to be detected enters into the sensor. The sensor housing can, for example, be formed of a metal or any other suitable material. Polymer or plastics are also examples of suitable materials for the housing.

The electrodes can comprise independently, the same or different, a metal selected from the group of Cu, Ni, Ti, Pt, Ir, Au, Pd, Ag, Ru, Rh, an oxide of Cu, Ni, Ti, Pt, Ir, Au, Pd, Ag, Ru, or Rh, mixtures thereof, or carbon, such as graphite, in particular graphite, Cu, Ag. As described above, the electrochemical gas sensors can be a two or three electrode system.

A two electrode system comprises one working electrode and one counter electrode. A three electrode system further includes a reference electrode.

It is furthermore preferred if the gas sensor is used for detection/measurement of gases selected from the group of acid gases, basic gases, neutral gases, oxidizing gases, reducing gases, halogen gases, halogen vapours, and hydride gases.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

BRIEF DESCRIPTION OF THE DRAWINGS

The invention is explained in more details by means of examples with reference to the figures. It shows.

DESCRIPTION OF THE INVENTION

Figure 1:
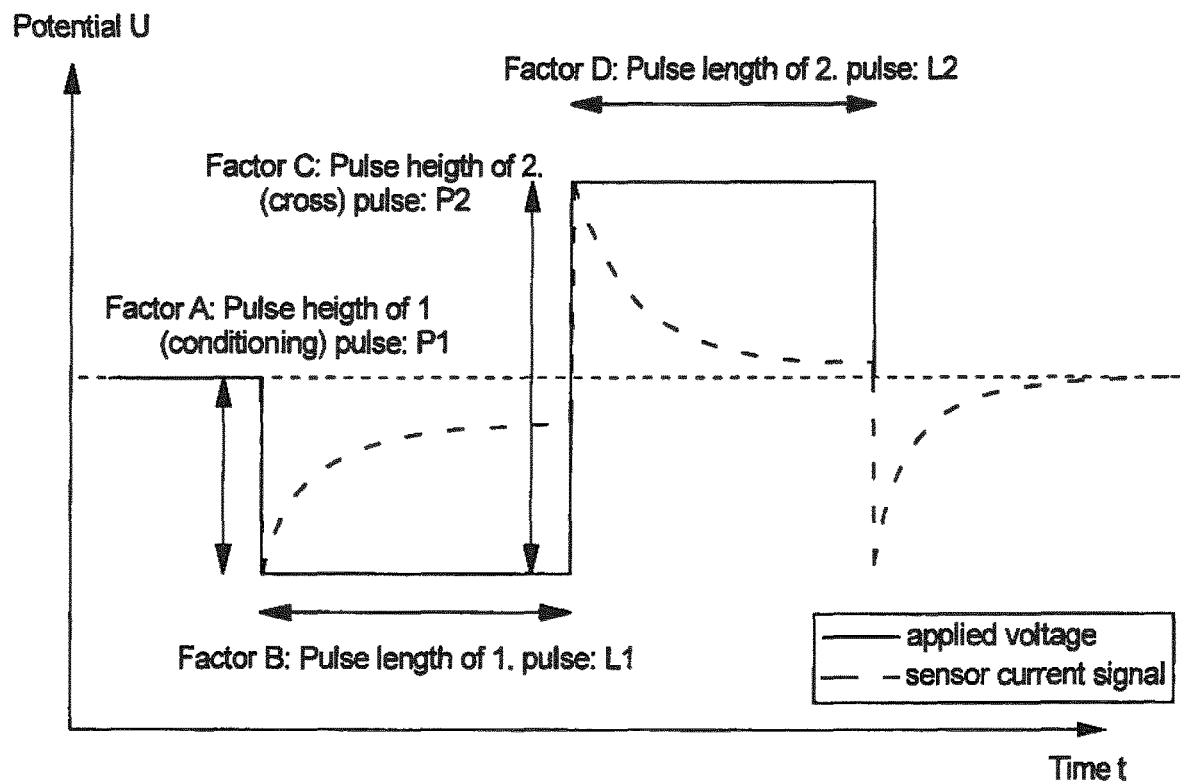
FIG. 1 is a first diagram illustrating the current pattern in response of the gas sensor to two electrical pulses.

For the purposes of the following detailed description, it is to be understood that the invention may assume various alternative variations and step sequences, except where expressly specified to the contrary. It is also to be understood that the specific compositions, coated substrates, multilayer coatings and methods described in the following specification are simply exemplary embodiments of the invention. Moreover, other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and attached claims are approximations that may vary depending upon the desired properties to be obtained by the present invention. At the very least, and not as an attempt to limit the application of the Doctrine of Equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

It is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting. Certain preferred and non-limiting embodiments or aspects of the present invention will be described with reference to the accompanying figures where like reference numbers correspond to like or functionally equivalent elements.

In this application, the use of the singular includes the plural and plural encompasses singular, unless specifically stated otherwise. In addition, in this application, the use of "or" means "and/or" unless specifically stated otherwise, even though "and/or" may be explicitly used in certain instances. Further, in this application, the use of "a" or "an" means "at least one" unless specifically stated otherwise.

The diagram of FIG. 1 illustrates the current pattern in response of the gas sensor to two electrical pulses. The two pulses are in each case characterized by their pulse height, pulse length, pulse direction, and pulse type. In the case of FIG. 1, a first pulse is applied to a predetermined pulse height, for example, between 5-15 mV for 1-10 sec and a second opposite pulse with a pulse height, for example, between 20-40 mV is applied for 1-10 sec. This is followed by the sensor reaction getting back to its original potential.

Figure 2:
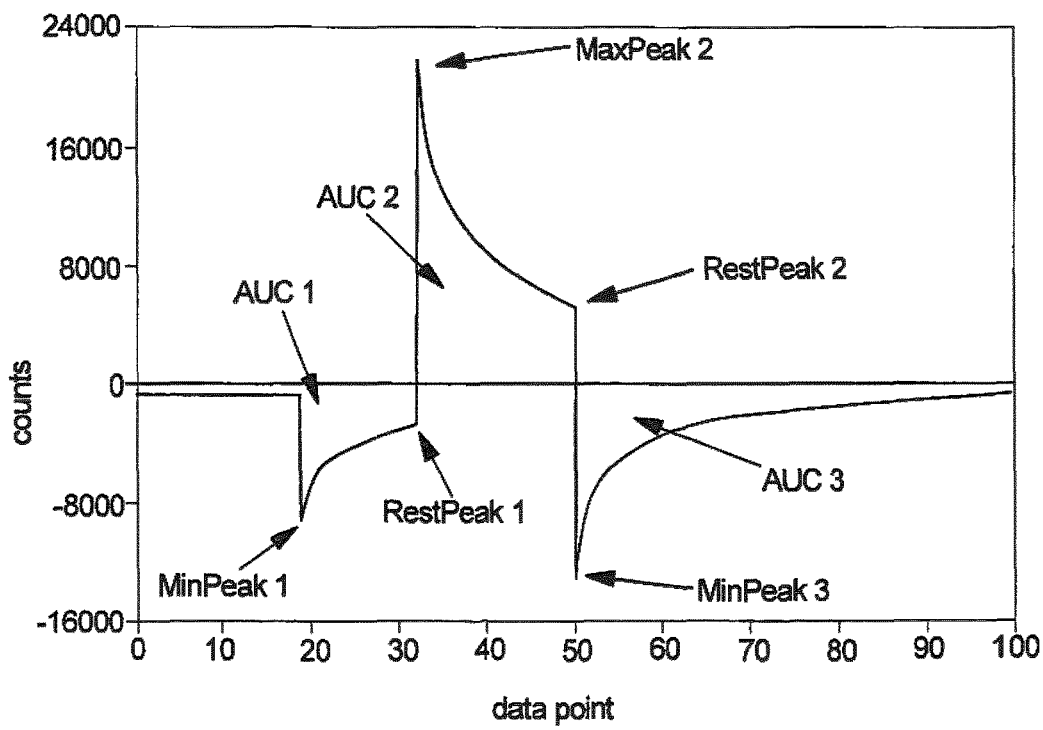
FIG. 2 is a second diagram illustrating the current pattern in response of the gas sensor to two electrical pulses with designated parameters.

In the diagram of FIG. 2, specific parameters are designated to the current curve or current pattern induced by the two voltage peaks in the gas sensor. The parameters are: minimal peak (corresponding to pulse height) of a first pulse P1, a resting peak of the first pulse P1 (RestPeak 1), the area under curve of the first pulse (AUC1), a maximal peak (corresponding to pulse height) of a second pulse P2, a resting peak of second pulse P2 (RestPeak 2), the area under curve of the second pulse (AUC2), minimal peak corresponding to sensor recovery height (MinPeak3 initial), and the area under the recovery curve (AUC3). These parameters are used in a specific algorithm for determining the calculated sensitivity of the sensor.

Figure 3:
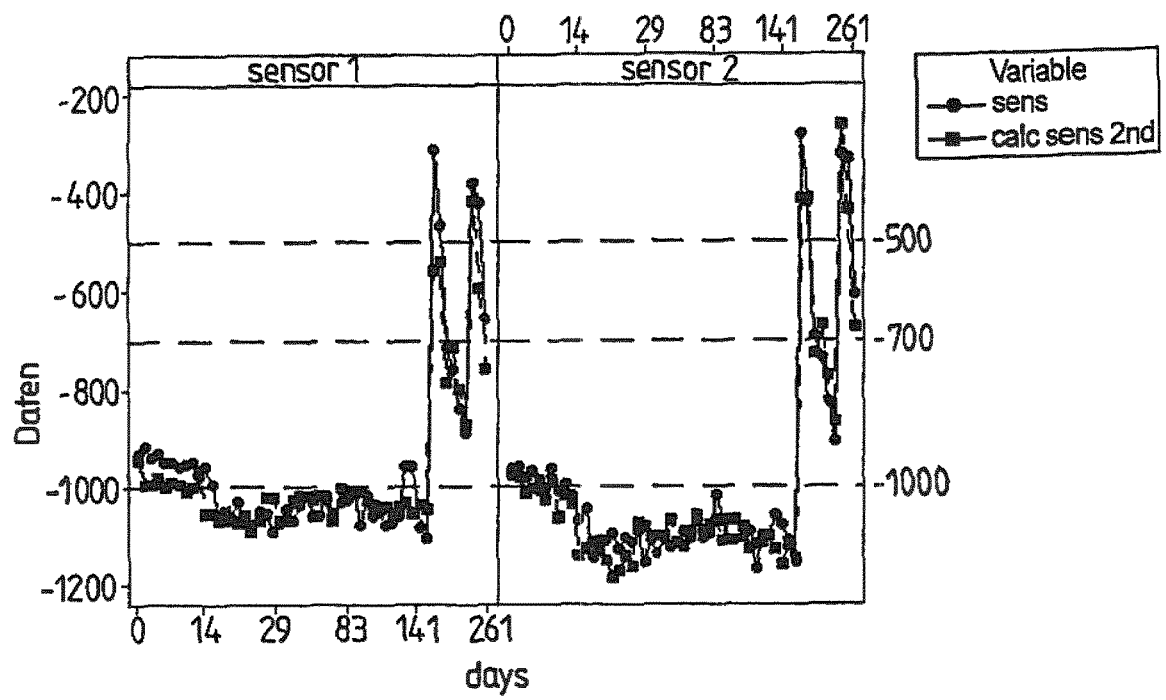
FIG. 3 is a third diagram illustrating the course of the sensitivity calculated according to the present method applying a complex model (calc sens 2nd) and of the measured sensitivity (sens) for two gas sensors.
Figure 4:
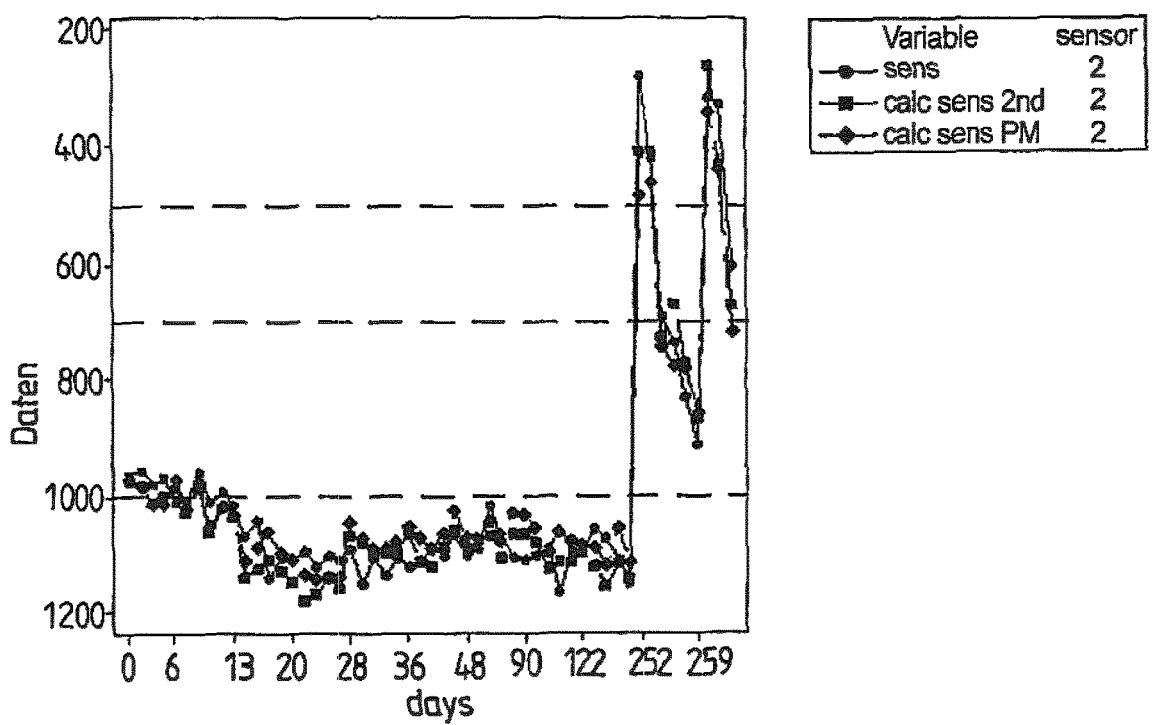
FIG. 4 is a fourth diagram illustrating the course of the sensitivity calculated according to the present method applying a complex model (calc sens 2nd) and a simplified model (calc sens PM) and of the measured sensitivity (sens)
Figure 5:
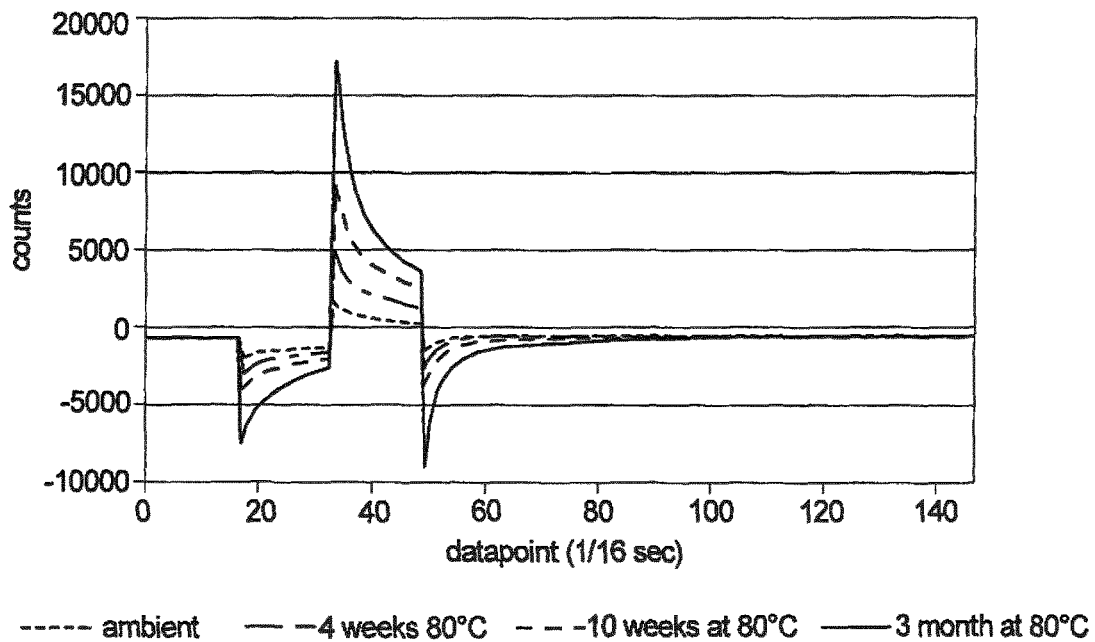
FIG. 5 is a fifth diagram illustrating the current pattern in response of the gas sensor to two or three electrical pulses when stored at 80° C.

The diagram of FIG. 3 illustrates the course of the sensitivity calculated according to the present method applying a complex model (calc sens 2nd) and of the measured sensitivity (sens) for two gas sensors;

The diagram of FIG. 4 illustrates the course of the sensitivity calculated according to the present method applying a complex model (calc sens 2nd) and a simplified model (calc sens PM) and of the measured sensitivity (sens);

The diagram of FIG. 5 illustrates the current pattern in response of the gas sensor to two electrical pulses when stored at 80° C. for 4 weeks, 10 weeks and 3 months, respectively. The long term storage causes a sensitivity loss. The current flow decreases gradually within the storage period of 3 months until no current is generated any longer.

Figure 6:
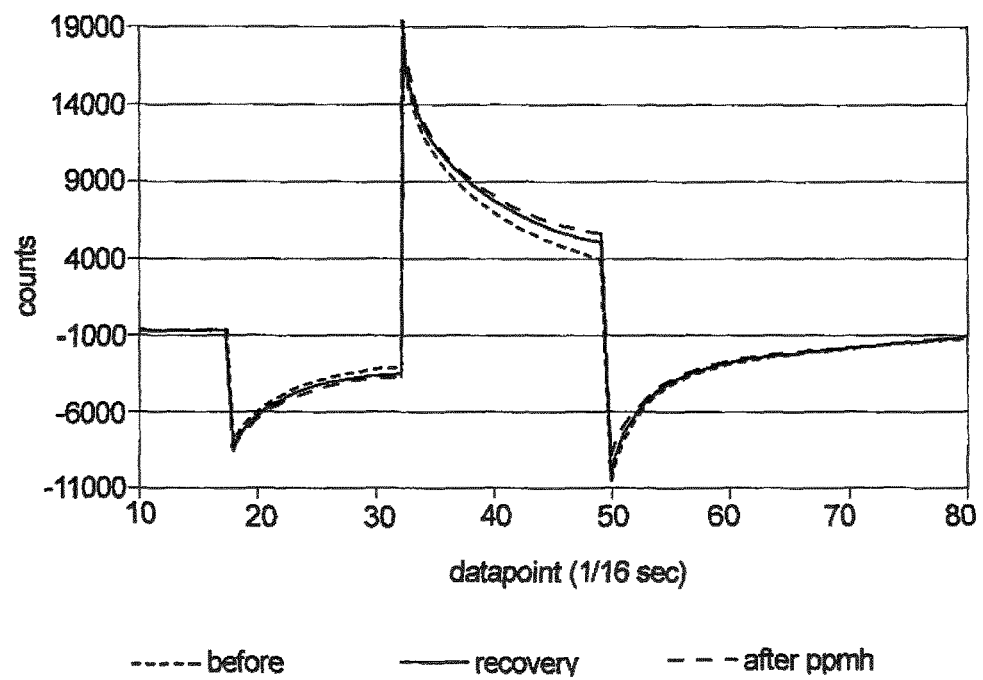
FIG. 6 is a sixth diagram illustrating the current pattern in response of the gas sensor to two or three electrical pulses when overgassed including the recovery behavior after overgassing.

The diagram of FIG. 6 illustrates the current pattern in response of the gas sensor to two electrical pulses when overgassed. Specifically the gas sensor is gassed with a high concentration of $Cl_2$ gas. This causes a slower signal (current) decrease probably due to a reversible adhesion of the gas molecules to the surface of the graphite electrode.

Example

The calculation is based on the current response to the sensor to an applied voltage pulse (see also FIG. 1). The current response can be divided in 8 parameters that are recorded independently from each other during the experiment. The 8 parameters are depicted in the diagram of FIG. 2.

a) Calibration

A first calibration of the sensor comprises the recording of a first voltage pulse and gassing with the target gas (in this case 10 ppm $Cl_2$) in order to determine the actual gas sensitivity of the sensor. In the specific example, the calibration measurement provided the following parameters shown in Table 1 (all parameters except the initial sensitivity are provided without any unit since values digitally converted by the sensor electronic are used).

TABLE 1

| Parameter (t0) | Abbreviation | Value for sensor 1 at day 0 | Value for sensor 2 at day 0 |
| --- | --- | --- | --- |
| Initial Sensitivity | Sens initial | −932 nA/ppm | −965 nA/ppm |
| MinPeak 1 initial | MP1 initial | −7689.7 | −7739.6 |
| MaxPeak2 initial | MP2 initial | 21032.3 | 21162.4 |
| MinPeak3 initial | MP3 initial | −10781.7 | −11277.6 |
| RestPeak1 initial | RP1 initial | −1718.7 | −1454.6 |
| RestPeak2 initial | RP2 initial | 4457.3 | 3761.4 |
| AreaUnderCurve 1 initial | AUC1 initial | −54723.0 | −51718.0 |
| AreaUnderCurve 2 initial | AUC2 initial | 144726.0 | 136475.0 |
| AreaUnderCurve 3 initial | AUC3 initial | −90415.0 | −81775.0 | b) Recording of Data for Modelling

The previous test is repeated in regular intervals (applying the pulse and measuring the sensitivity by target gas calibration) and values for gas sensor sensitivity and the 8 parameters of the current response to the pulse are determined. This provides for every experiment a data set of the following parameters shown in Table 2.

TABLE 2

| Parameter (t1) | Abbreviation | Value for sensor 1 at day 13 | Value for sensor 2 at day 13 |
| --- | --- | --- | --- |
| Sensitivity | Sens | −978 nA/ppm | −1017 nA/ppm |
| MinPeak 1 | MP1 | −7688.9 | −7715.0 |
| MaxPeak2 | MP2 | 21061.1 | 21099.0 |
| MinPeak3 | MP3 | −10788.9 | −11268.0 |
| RestPeak1 | RP1 | −1693.9 | −1456.0 |
| RestPeak2 | RP2 | 4463.1 | 3746.0 |
| AreaUnderCurve 1 | AUC1 | −54533.0 | −51716.0 |
| AreaUnderCurve 2 | AUC2 | 145215.0 | 136440.0 |
| AreaUnderCurve 3 | AUC3 | −89705.0 | −83666.0 |

A difference of the values of Table 2 and the initial values of Table 1 is calculated in order to follow the change of the value over time.

Following general equation is applied: Δ parameter=parameter(t1)−parameter(t0).

Said differences are used for the actual sensitivity calculation and are shown in Table 3.

TABLE 3

| Parameter | Abbreviation | Value for sensor 1 at day 13 | Value for sensor 2 at day 13 |
| --- | --- | --- | --- |
| Change of Sensitivity | ΔSens | −46 nA/ppm | −52 nA/ppm |
| Change MinPeak 1 | ΔMP1 | 0.8 | 24.6 |
| Change MaxPeak2 | ΔMP2 | 28.8 | −63.4 |
| Change MinPeak3 | ΔMP3 | −7.2 | 9.6 |
| Change RestPeak1 | ΔRP1 | 24.8 | −1.4 |
| Change RestPeak2 | ΔRP2 | 5.8 | −15.4 |
| Change AreaUnderCurve 1 | ΔAUC1 | 190.0 | 2.0 |
| Change AreaUnderCurve 2 | ΔAUC2 | 489.0 | −35.0 |
| Change AreaUnderCurve 3 | ΔAUC3 | 710.0 | −1891.0 |

In this way, multiple pair of values were recorded over 260 days while the gas sensors were stored at different environmental conditions in order to cause sensitivity fluctuations. Some sensors were stored at 10% humidity, 85% humidity, or at normal humidity. Besides, some sensors were exposed to high chlorine concentrations in order to cause a reduction of sensitivity (the overloading with high chlorine concentrations is a known error modus of the sensors).

c) Modelling

The above set of data was subjected to a multi-linear regression in order to determine a correlation between the change of sensitivity and the change of parameters. Thereby, the focus can be directed to the best possible regression (I) or to a simplified model (II).

I. Best Regression

The time course of the Δ-values were used as input and the change of sensitivity was used as output and different models were tested. The calculated sensitivity ("calc sens") is correlated to the actual sensitivity. The data processing and modelling were done using Minitab Version 16/17.

If a good adaptation of the values is desired, the following model is provided from the regression using 7 parameters ("2nd order complex model"):

Calculated Sensitivity 'calc sens'=Sens initial+ΔSens.

$$\Delta Sens = c + a_1 * \Delta MP1 + a_2 * \Delta MP3 + a_3 * \Delta RP2 + a_4 * \Delta AUC1 +$$
$$a_5 * \Delta AUC2 + a_6 * (\Delta MP2)^2 + a_7 * (\Delta MP3)^2 + a_8 * (\Delta RP2)^2 +$$
$$a_9 * \Delta MP1 * \Delta MP2 + a_{10} * \Delta MP2 * \Delta MP3 + a_{11} * \Delta MP2 * \Delta RP2 +$$
$$a_{12} * \Delta MP3 * \Delta RP2 + a_{13} * \Delta RP1 * \Delta AUC1 + a_{13} * \Delta RP1 * \Delta AUC2$$

Following constants and factors were used for the model that provide the highest accuracy of prediction:

| Factor | Value for '2nd order complex model' |
|---|---|
| C | −12.36 |
| $a_1$ | 1.578 |
| $a_2$ | 2.224 |
| $a_3$ | −1.612 |
| $a_4$ | −0.1013 |
| $a_5$ | −0.04842 |
| $a_6$ | −0.005888 |
| $a_7$ | −0.01461 |
| $a_8$ | −0.005588 |
| $a_9$ | −0.000852 |
| $a_{10}$ | −0.01814 |
| $a_{11}$ | 0.01127 |
| $a_{12}$ | 0.01859 |
| $a_{13}$ | −0.000112 |
| $a_{14}$ | −0.000075 |

This model provides a high correlation (R2 corrected=72.8%) of the sensitivities exclusively calculated based on pulse data and calibration values and the measured sensitivity.

For the example, the sensors course of measured and exclusively calculated sensitivities are shown in the diagram of FIG. 3. Here, each point in the diagram corresponds to a measured value recording, i.e., applying the pulse and measuring sensitivity at a certain day. As can be seen in the diagram of FIG. 3, both sensors show good correlations between measured sensitivity ("sens") and sensitivity calculated with the "2nd order complex model" ("calc sens 2nd").

II. Simplified Model

Since the values of the curve areas require a calculation, the model can be simplified by using only punctual values of the current response curve for modelling and regression (PM=point-model).

This provides a simplified model using 5 parameters:

$$Sens(PM) = Sens\ \text{initial} + \Delta Sens(PM)$$

$$\Delta Sens(PM) = c + a_1 * \Delta MP1 + a_2 * \Delta MP2 + a_3 * \Delta MP3 + a_4 * \Delta RP1 +$$
$$a_5 * \Delta RP2 + a_6 * (\Delta MP1)^2 + a_7 * (\Delta MP3)^2 + a_8 * \Delta MP1 * \Delta MP3 +$$
$$a_9 * \Delta MP1 * \Delta RP2 + a_{10} * \Delta MP2 * \Delta RP1 + a_{11} * \Delta MP2 * \Delta RP2 +$$
$$a_{12} * \Delta MP3 * \Delta RP1 + a_{13} * \Delta MP3 * \Delta RP2 + a_{14} * \Delta RP1 * \Delta RP2$$

The following constants and factors are used for the "point-model":

| Factor | Values for '2nd order point model' |
|---|---|
| C | −6.93 |
| $a_1$ | −0.821 |
| $a_2$ | 1.578 |
| $a_3$ | 2.675 |
| $a_4$ | −1.139 |
| $a_5$ | 2.5 |
| $a_6$ | −0.02731 |
| $a_7$ | −0.008428 |
| $a_8$ | 0.03046 |
| $a_9$ | −0.02787 |
| $a_{10}$ | −0.01059 |
| $a_{11}$ | −0.006318 |
| $a_{12}$ | −0.01663 |
| $a_{13}$ | 0.005691 |
| $a_{14}$ | 0.01199 |

Even though this simplification does not reduce the number of factors, however, the calculations of the curve areas are not required. Furthermore, the minimal required pulse length can be reduced since only singular point values and not time depending areas are used in the model.

The correlation of the calculated sensitivity using the simplified point model and the measured sensitivity for the example sensors is shown in the diagram of FIG. 4. Here, the measured sensitivity ("sens"), the calculated sensitivity using the 2nd order complex model ("calc sens 2nd"), and the calculated sensitivity using the 2nd order point model ("calc sens PM") are illustrated and compared.

By reducing the parameters from 7 to 5, a deterioration of the model quality can be seen in the overall correlation. The accuracy of the regression (determined based on the R2 corrected value) is reduced from 72.8% to 68.6%. However, the course of sensitivity still shows a very good correlation.

As can be seen, disclosed is an electrochemical method for determining the sensitivity of at least one gas sensor comprising: applying at least two electrical pulses to at least two parts of at least two electrodes of the gas sensor, recording a change of a current pattern induced in the at least two electrodes by the at least two pulses over time, calculating at least one value for the sensor sensitivity by applying an algorithm to the current pattern induced by the at least two pulses, and comparing the calculated sensitivity value to known gas sensitivity calibration data.

The at least two pulses can be voltage pulses.

The at least two pulses can be varied by one of the following pulse parameters: pulse height (mV), pulse length (sec), and type of pulse.

The parameters can be the same or different for each of the at least two pulses.

The at least two electrical pulses can be applied in opposite directions to the gas sensor.

A sequence of more than two electrical pulses can be applied to the at least one gas sensor.

A sequence of four or more electrical pulses can be applied to the at least one gas sensor.

The current pattern induced by the at least two pulses can be described by at least 2, or 5, or 7, or 8 parameters.

The current pattern induced by the at least two pulses can be described by one of the following parameters: a maximal or minimal peak (corresponding to pulse height) of a first pulse P1, a resting peak of a first pulse P1 (RestPeak 1), an area under curve of the first pulse (AUC1), a maximal or minimal peak (corresponding to pulse height) of a second pulse P2, a resting peak of the second pulse P2 (RestPeak 2), and an area under curve of the second pulse (AUC2).

The algorithm for calculating the at least one value for the sensor sensitivity can be generated based on the at least 2 parameters of the current pattern induced by the at least two pulses.

The gas sensitivity calibration data can be previously obtained from the same gas sensor type.

The at least one gas sensor can comprise an electrolyte selected from a group comprising: at least one ionic liquid with at least one additive portion; an aqueous salt solution; a mineral acid; a base; and an organic salt solution.

The aqueous salt solution can be an aqueous LiCl solution. The mineral acid can be $H_2SO_4$ or $H_3PO_4$. The base can be KOH. The organic salt can be $LiPF_6$ in dimethylcarbonate glycol and/or ethylenecarbonate glycol.

The at least one additive portion can comprise at least one organic additive, at least one organometallic additive, or at least one inorganic additive.

The sensor can comprise at least two electrodes in electrical contact with the ionic liquid. The electrodes can be separated from one another by a separator or by space.

The electrodes can comprise independently, the same or different: a metal selected from the group of Cu, Ni, Ti, Pt, Ir, Au, Pd, Ag, Ru, Rh, an oxide of Cu, Ni, Ti, Pt, Ir, Au, Pd, Ag, Ru, or Rh, and mixtures thereof, or carbon such as graphite.

The gas sensor can be adapted for the detection of gases selected from the group of acid gases, basic gases, neutral gases, oxidizing gases, reducing gases, halogen gases, halogen vapors, and hydride gases.

Finally, the gas sensor can be adapted for the detection of gases selected from the group of $F_2$, $Cl_2$, $Br_2$, $I_2$, $O_2$, $O_3$, $ClO_2$, $NH_3$, $SO_2$, $H_2S$, CO, $CO_2$, NO, $NO_2$, $H_2$, HCl, HBr, HF, HCN, $PH_3$, $AsH_3$, $B_2H_6$, $GeH_4$, and $SiH_4$.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. An electrochemical method for determining the sensitivity of at least one gas sensor comprising:
    applying at least two electrical pulses to at least two parts of at least two electrodes of at least one gas sensor, wherein the at least two electrical pulses comprise a first pulse and a second pulse;
    recording a change of a plurality of parameters over time in a current pattern induced in the at least two electrodes by the at least two pulses over time, wherein the current pattern induced by the at least two pulses is described by the plurality of parameters, and wherein the plurality of parameters comprises:
        an area under curve of the current pattern based on the first pulse (AUC1), and
        an area under curve of the current pattern based on the second pulse (AUC2);
    calculating at least one sensitivity value for the at least one gas sensor by applying an algorithm to the change of the plurality of parameters over time in the current pattern induced by the at least two pulses; and
    comparing the at least one calculated sensitivity value to known gas sensitivity calibration data.

2. The method according to claim 1, wherein the at least two pulses are voltage pulses.

3. The method according to claim 1, wherein the at least two pulses are varied from each other by at least one of pulse height (mV), pulse length (sec), or type of pulse.

4. The method according to claim 3, wherein the plurality of parameters, for which the change is recorded, are the same or different based on each of the at least two pulses.

5. The method according to claim 1, wherein the at least two electrical pulses are applied in opposite directions to the at least one gas sensor.

6. The method according to claim 1, wherein a sequence of more than two electrical pulses is applied to the at least one gas sensor.

7. The method according to claim 1, wherein a sequence of four or more electrical pulses is applied to the at least one gas sensor.

8. The method according to claim 1, wherein the current pattern induced by the at least two pulses is described by at least 2 parameters.

9. The method according to claim 8, wherein the algorithm for calculating the at least one sensitivity value for the at least one gas sensor is generated based on the at least 2 parameters of the current pattern induced by the at least two pulses.

10. The method according to claim 1, wherein the current pattern induced by the at least two pulses is described by at least 8 parameters.

11. The method according to claim 1, wherein the plurality of parameters further comprises one of the following parameters:
    a maximal or minimal peak of the current pattern corresponding to pulse height of the first pulse;
    a resting peak of the current pattern based on a first pulse (RestPeak 1);
    a maximal or minimal peak of the current pattern corresponding to pulse height of the second pulse; or
    a resting peak of the current pattern based on the second pulse (RestPeak 2).

12. The method according to claim 1, wherein the gas sensitivity calibration data are previously obtained from the same gas sensor type.

13. The method according to claim 1, wherein the at least one gas sensor comprises an electrolyte selected from a group comprising:
    at least one ionic liquid with at least one additive portion;
    an aqueous salt solution;
    a mineral acid;
    a base; and
    an organic salt solution.

14. The method according to claim 13, wherein:
    the aqueous salt solution is an aqueous LiCl solution;
    the mineral acid is $H_2SO_4$ or $H_3PO_4$;
    the base is KOH; or
    the organic salt solution comprises $LiPF_6$ in dimethylcarbonate glycol and/or ethylenecarbonate glycol.

15. The method according to claim 13, wherein the at least one additive portion comprises at least one organic additive, at least one organometallic additive, or at least one inorganic additive.

16. The method according to claim 13, wherein the at least one gas sensor comprises the at least two electrodes being in electrical contact with the at least one ionic liquid, the at least two electrodes being separated from one another by a separator or by space.

17. The method according to claim 1, wherein the electrodes comprise independently, the same or different:
    a metal selected from the group of Cu, Ni, Ti, Pt, Ir, Au, Pd, Ag, Ru, Rh;
    an oxide Cu, Ni, Ti, Pt, Ir, Au, Pd, Ag, Ru, or Rh and mixtures thereof or carbon.

18. The method according to claim 17, wherein the carbon comprises graphite.

19. The method according to claim 1, wherein the gas sensor is adapted for the detection of gases selected from the group of acid gases, basic gases, neutral gases, oxidizing gases, reducing gases, halogen gases, halogen vapors, and hydride gases.

20. The method according to claim 1, wherein the gas sensor is adapted for the detection of gases selected from the group of $F_2$, $Cl_2$, $Br_2$, $I_2$, $O_2$, $O_3$, $ClO_2$, $NH_3$, $SO_2$, $H_2S$, $CO$, $CO_2$, $NO$, $NO_2$, $H_2$, $HCl$, $HBr$, $HF$, $HCN$, $PH_3$, $AsH_3$, $B_2H_6$, $GeH_4$, and $SiH_4$.

* * * * *